United States Patent [19]

Bielefeldt et al.

[11] Patent Number: 4,902,839

[45] Date of Patent: Feb. 20, 1990

[54] PROCESS FOR PREPARING FLUORINATED $C_4$ TO $C_6$ HYDROCARBONS AND NOVEL CYCLIC FLUORINATED HYDROCARBONS AND THEIR USE AS PROPELLANT GAS AND WORKING FLUID FOR HEAT PUMP SYSTEMS

[75] Inventors: Dietmar Bielefeldt, Ratingen; Albrecht Marhold, Leverkusen; Michael Negele, Cologne, all of Fed. Rep. of Germany

[73] Assignee: Bayer Aktiengesellschaft, Bayerwerk, Fed. Rep. of Germany

[21] Appl. No.: 257,351

[22] Filed: Oct. 13, 1988

[30] Foreign Application Priority Data

Oct. 20, 1987 [DE] Fed. Rep. of Germany ....... 3735467

[51] Int. Cl.[4] ............................................. C07C 19/08
[52] U.S. Cl. ..................................................... 570/175
[58] Field of Search ........................................ 570/175

[56] References Cited

U.S. PATENT DOCUMENTS 2,550,953  5/1951  Barrick ................................ 570/175

FOREIGN PATENT DOCUMENTS 3725213  of 0000  Fed. Rep. of Germany .
1401541  2/1972  United Kingdom .

OTHER PUBLICATIONS

Huang et al, Youji Hauxve, 2, 125-128 (1984) English translation.
Preparation, Properties, and Technology of Fluorine and Organic Fluoro Compounds, Slesser/Schram (McGraw-Hill 1951) p. 817.
Tetrahedron, 4217-4224 (1969).
J. Chem. Soc., 387-396 (1959) Haezeldine and Nyman.
J. Chem. Soc., 1673-1677 (1952), N. B. Chapman and J. L. Levy.
J. Org. Chem., 51 (3228-3231 (1986)—D. P. Matthews et al.
Reagents for Organic Synthesis, vol. 1 (John Wiley & Sons, 1967) p. 723, Fieser and Fieser.
Y. Huang et al., *Youji Huaxve,* 2, 125, 2, 125 (1984).
F. S. Rowland et al., *Nature,* 249, 8 (1974).
Abstract of PL Inventor's Certificate 87,481, Nov. 30, 1976.
R. N. Hazeldine, Journal of Chemical Society, p. 2504, 1952.
D. D. Coffman et al, Journal of American Chemical Society, vol. 71, p. 490, 1949.
H. L. Henne et al., Journal of American Chemical Society, vol. 67, p. 1235, 1945.
H. L. Henne et al, Journal of American Chemical Society, vol. 73, p. 1103, 1951.
J. F. D. Mills, Cellular Polymers 5, 1986, pp. 343-355.

*Primary Examiner*—Alan Siegel
*Attorney, Agent, or Firm*—Joseph C. Gil; Richard E. L. Henderson

[57] ABSTRACT

This invention relates to a process for preparing fluorinated $C_4$ to $C_6$ hydrocarbons by catalytically hydrogenating, in the presence of a base, at least partially halogenated olefins. This invention also relates to certain novel cyclic fluorinated $C_5$ and $C_6$ hydrocarbons prepared by the process of this invention. This invention further relates to the use of fluorinated $C_4$ to $C_6$ hydrocarbons as propellant gas or as working fluid for heat pump systems.

10 Claims, No Drawings

PROCESS FOR PREPARING FLUORINATED C₄ TO C₆ HYDROCARBONS AND NOVEL CYCLIC FLUORINATED HYDROCARBONS AND THEIR USE AS PROPELLANT GAS AND WORKING FLUID FOR HEAT PUMP SYSTEMS

BACKGROUND OF THE INVENTION

The present invention relates to the preparation of linear and cyclic fluorinated C₄ to C₆ hydrocarbons by catalytic hydrogenation of appropriate haloolefins, to novel cyclic fluorinated hydrocarbons, and to the use of fluorinated C₄ to C₆ hydrocarbons as propellant gas and working fluid for heat pump systems.

Processes for preparing special fluorinated C₄ hydrocarbons are known. Thus, 1,1,1,4,4,4-hexafluorobutane can be prepared by reacting succinic acid with sulfur tetrafluoride. W. Dmowski et al, PL Inventor's Certificate 87,481. This process is unsatisfactory since it requires sulfur tetrafluoride, which is not only toxic but is accessible only by an uneconomical method. 1,1,1,4,4,4-Hexafluorobutane can also be prepared by hydrogenating 1,1,1,4,4,4-hexafluoro-2-chloro-2-butene or 1,1,1,4,4,4-hexafluoro-2,3-dichloro-2-butene catalytically in the presence of palladium on aluminum oxide (Y. Huang et al, *Youji Huaxve*, 2, 125 (1984)), but the product of this process is always obtained in the form of mixtures with chlorine-containing compounds. However, according to more recent reports (see J. F. D. Mills, *Cell. Polym.*, 5, 343 (1987) and F. S. Rowland et al, *Nature*, 249, 8 (1974)), the chlorine contained in conventional propellant gases causes damage to the ozone layer of the earth's atmosphere. Finally, 1,1,1,4,4,4-hexafluorobutane can also be prepared by hydrogenation of 1,1,1,4,4,4-hexafluoro-2-butene. R. N. Haszeldine, *J. Chem. Soc.*, 2504 (1952). The disadvantage of this process is that a difficulty obtained and expensive starting material must be used. R.N. Haszeldine, *J. Chem. Soc.*, 2504 (1952).

1,1,2,2-Tetrafluorocyclobutane can be prepared by reaction of tetrafluoroethylene with ethylene in a "two +two" addition. D. Coffman et al, *J. Amer. Chem. Soc.*, 71, 490 (1949). However, the yield of this reaction is not satisfactory.

SUMMARY OF THE INVENTION

The present invention relates to a process for preparing fluorinated C₄ to C₆ hydrocarbons of the formula (I)

wherein $R_f$ is $CF_3$ or the two $R_f$ groups taken together are —$CF_2$—$CF_2$—, —$CF_2$—$CF_2$—$CF_2$—, or —$CH(CF_3)$—$CH(CF_3)$—, comprising catalytically hydrogenating, in a presence of suitable base, olefinic compounds of the formula (II)

wherein
X is hydrogen, fluorine, chlorine, or bromine;
Y is fluorine, chlorine, or bromine; and
$R_f$ has the meaning given under the formula (I).

DETAILED DESCRIPTION OF THE INVENTION

Suitable olefinic compounds of the formula (II) of this invention include, for example, 1,1,1,4,4,4-hexafluoro-2-chloro-2-butene, 1,1,1,2,4,4,4-heptafluoro-2-butene, 1,1,1,4,4,4-hexafluoro-2,3-dichloro-2-butene, 3,3,4,4-tetrafluoro-1-chlorocyclobutene, 3,3,4,4-tetrafluoro-1,2-dichlorocyclobutene, 3,3,4,4,5,5-hexafluoro-1-chlorocyclopentene, 3,3,4,4,5,5-hexafluoro-1,2-dichlorocyclopentene, 3,4-di(trifluoromethyl)-1-chlorocyclobutene, 3,4-di(trifluoromethyl)-1,2-dichlorocyclobutene, 1,1,1,4,4,4-hexafluoro-2,3-dibromo-2-butene and 1,1,1,4,4,4-hexafluoro-2-bromo-3-chloro-2-butene.

It is not absolutely necessary to start with olefinic compounds of the formula (II). It is also possible to start with precursors which give compounds of the formula (II) as intermediates. Precursors of compounds of the formula (II), can be, for example, compounds of the formula (III)

wherein each X and each Y independently of one another and $R_f$ have the meaning given under the formula (I) or (II). The compounds of the formula (III) can be converted to compounds of the formula (II), for example, by elimination of hydrogen halide. If desired, such an elimination reaction can be preceded by the exchange of halogen for hydrogen. Examples of compounds of the formula (III) include 1,1,1,4,4,4-hexafluoro-2,2,3-trichlorobutane, 1,1,1,4,4,4-hexafluoro-2,2,3,3-tetrachlorobutane and 1,1,1,4,4,4-hexafluoro-2,3-dibromo2-chlorobutane.

Preferred starting compounds used in the process according to the invention include the following compounds of the formula (II): 1,1,1,4,4,4-hexafluoro-2chlorobutene, 3,3,4,4-tetrafluoro-1,2-dichlorocyclobutene, 3,3,4,4,5,5-hexafluoro-1,2-dichlorocyclopentene and 1,1,1,2,4,4,4-heptafluoro-2-butene.

The starting compounds for the process according to the invention are readily accessible, using, for example, the method according to German Offenlegungsschrift 3,725,213, or H. L. Henne et al, *J. Am. Chem. Soc.*, 67, 1235 (1945), and 73, 1103 (1951).

Suitable hydrogenation catalysts for the process according to the invention include metals or metal-containing materials. Suitable examples include the metals of transition group VIII of the periodic table of the elements, especially palladium, platinum and nickel.

The metals can be used in elemental form or in the form of compounds (for example, as oxides or hydroxides). The metals can also be used in specially activated forms, for example, in the form of Raney metals, or applied to a carrier material. Preference is given to Raney nickel or palladium on carbon, aluminum oxide, silica, barium sulphate, calcium carbonate, lithium aluminum spinel, silica gel or magnesium oxide. It is also possible to use catalysts which contain two or more metals, for example nickel and iron. The catalysts can also be doped with additives in any desired manner.

In general, the amount of catalyst is not critical. For example, 1 to 100% by weight of catalyst, based on the compound of the formula (II) used, can be used. The quantity of catalyst refers to the catalytically active component of the catalysts, so that if supported catalysts are used, the weight of the carrier material is not included when calculating the amount of catalyst to be used.

Suitable bases for the process according to the invention include a wide range of inorganic and organic alkaline compounds. Examples of such bases include the oxides, hydroxides, acetates, carbonates and bicarbonates of alkali metals and alkaline-earth metals, as well as tertiary amines. Preferred bases include potassium hydroxide, sodium hydroxide, sodium acetate, triethylamine, and pyridine.

The bases can be used in various amounts. If compounds of the formula (II) in which X is hydrogen are used, 0.8 to 1.2 equivalents of base per mol of the compound of the formula (II) are preferably used. If compounds of the formula (II) in which X is chlorine are used, 1.8 to 3 equivalents of base per mol of the compound of the formula (II) are preferably used.

The hydrogenation according to the invention can be carried out at various pressures and temperatures. Suitable pressures are, for example, those in the range of about 1 to 200 bar and suitable temperatures are those in the range of about 0° to 200° C. Preference is given to pressures in the range of about 1 to 60 bar and to temperatures in the range of about 20° to 60° C.

The process according to the invention is preferably carried out in the presence of a solvent. Suitable solvents include, for example, alcohols such as methanol and ethanol, ethers such as tetrahydrofuran and diglyme, aromatics such as toluene, and alkanoic acids such as acetic acid.

The process can be carried out not only batchwise but also continuously. In the case of continuous operation, the catalyst is preferably arranged in a fixed bed.

The reaction mixture can, for example, be worked up by first removing any solids present and then stripping the solvent from the filtrate. It can also be worked up by pouring the reaction mixture freed from the catalyst onto ice water, separating the resulting organic phase, and then fractionally distilling the organic phase. The reaction mixture can also be worked up by any number of other methods known in the art.

The process according to the invention has several advantages. For example, the process requires no starting materials and reagents which are difficult to obtain, it affords pure products in good yield, and it provides an economical route to fluorinated, but chlorine-free, hydrocarbons.

The present invention further relates to novel cyclic fluorinated hydrocarbons of the formula (Ia)

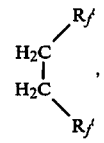
(Ia)

wherein the two $R_f'$ groups taken together are $-CF_2-CF_2-CF_2-$ or $-CH(CF_3)-CH(CF_3)-$; that is, 1,1,2,2,3,3-hexafluorocyclopentane and 1,2-di(trifluoromethyl)cyclobutane. A process for preparing the novel compounds of the formula (Ia) is described above and possibilities for industrial use are described below.

The present invention further relates to the use as propellant gas of compounds of the formula (I)

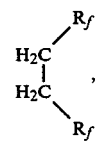
(I)

wherein $R_f$ is $CF_3$ or the two $R_f$ groups taken together are $-CF_2-CF_2-$, $-CF_2-CF_2-CF_2-$ or $-CH(CF_3)-CH(CF_3)-$.

Preferably, these compounds can be used as propellant gas for sprays having a wide range of uses, for example, as sprays for cosmetic purposes (such as deodorant sprays). Particularly preferably, these compounds can be used as propellant gas in sprays used for medical purposes, for example, in sprays for asthmatics or in liquid plaster sprays. For such uses, particular preference is given to 1,1,1,4,4,4-hexafluorobutane.

Sprays which, according to the present invention, contain compounds of the formula (I) as propellant gas are inert and nonflammable, as are the fluorinated and chlorinated hydrocarbons which hitherto have frequently been used for this purpose. However, because the compounds of formula (I) are chlorine-free, these compounds have the additional advantage of leaving virtually unaffected the ozone layer of the earth's atmosphere.

The present invention also relates to the use as working fluid for heat pump systems of compounds of the formula (Ib)

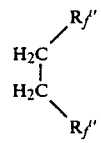
(Ib)

wherein $R_f''$ is $CF_3$ or the two $R_f''$ groups taken together are $-CF_2-CF_2-CF_2-$ or $-CH(CF_3)-CH(CF_3)-$.

The present invention, which is set forth in the foregoing disclosure, is not to be construed or limited either in spirit or in scope by these examples. Those skilled in the art will readily understand that known variations of the conditions and processes of the following preparative procedures can be used. In the following examples, all percentages are percentages by weight and all temperatures are degrees Celsius unless otherwise noted.

EXAMPLES

EXAMPLE 1

In a stainless steel autoclave, 40 g of 1,1,1,4,4,4-hexafluoro-2-chloro-2-butene in 300 ml of ethanol were hydrogenated with hydrogen in the presence of 12 g of potassium hydroxide and 25 g of Raney nickel for 3 hours at 20° C. and another 1 hour at 100° C. at a pressure of from 30 to 40 bar. The solid components were then removed from the reaction mixture by filtration and the remaining liquid was distilled to give 16 g of 1,1,1,4,4,4-hexafluorobutane having a boiling point of 25°–30° C. at 1013 mbar. The mass spectrum showed a molecular ion at m/e 166.

EXAMPLE 2

199 g (1 mol) of 1,1,1,4,4,4-hexafluoro-2-chloro-2-butene were hydrogenated in 800 ml of diglyme in the presence of 45 g of sodium hydroxide and 30 g of Raney nickel in the temperature range from 20° to 40° C. and at a hydrogen pressure of 20 to 40 bar. The solid components were filtered off, the solvent was extracted with water, and the organic phase was separated and purified by fractional distillation. The yield of 1,1,1,4,4,4-hexafluorobutane was 125 g (75% of theory). The boiling point was 24°–27° C. at 1013 mbar. The $^{19}$F—NMR spectrum showed one peak at $-10.7$ ppm ($CF_3CO_2H$ standard).

EXAMPLE 3

10 g (36 mmol) of 1,1,1,4,4,4-hexafluoro-2-bromo-3-chloro-2-butene were hydrogenated in 50 ml of tetrahydrofuran in the presence of 3.0 g of sodium hydroxide and 5 g of Raney nickel in the temperature range from 20° to 40° C and at a hydrogen pressure of 20 to 40 bar. The reaction mixture was worked up as described in Example 2. The yield was 3.5 g of 1,1,1,1,4,4,4,-hexafluorobutane (59% of theory).

EXAMPLE 4

40 g (0.2 mol) of 1,1,1,4,4,4-hexafluoro2-chloro-2-butene were hydrogenated in 300 ml of ethanol in the presence of 12 g of potassium hydroxide and 24 g of Raney nickel in the pressure range of from 20 to 40 bar and at a temperature from 20° to 100° C. The solid components were filtered off, the solvent was extracted with water, and the organic phase was separated and purified by distillation to give 15.5 g (47% of theory) of 1,1,1,4,4,4-hexafluorobutane. The boiling point was 25° to 27° C. at 1013 mbar.

EXAMPLE 5

50 ml of tetrahydrofuran, 8.5 g of sodium hydroxide and 3 g of 5% by weight palladium on carbon catalyst were added to 23.5 g (0.1 mol) of 1,1,1,4,4,4- hexafluoro-2,3-dichloro-2-butene. This mixture was hydrogenated with hydrogen at temperatures between 20° and 40° C. and at pressures in the range 20 to 40 bar. The reaction mixture was worked up as described in Example 2. The yield was 8.0 g (75% of theory) of 1,1,1,4,4,4-hexafluorobutane.

EXAMPLE 6

In a 1.3 l stainless steel autoclave, 245 g (1 mol) of 1,2-dichloro-3,3,4,4,5,5-hexafluorocyclopentene were hydrogenated at 60° to 70° C. with the addition of 202 g (2 mol) of triethylamine in 200 ml of methanol and in the presence of 20 g of Raney nickel. Over a period of 12 hours, the theoretical amount of hydrogen was absorbed at a hydrogen pressure of 40 to 50 bar. The reaction mixture was filtered and the methanolic solution was diluted with 400 ml of water. The lower organic phase was separated, washed with 100 ml of 5% aqueous hydrochloric acid, and dried over sodium sulfate. Distillation through a 1-m spinning band column gave 106 g (60% of theory) of 1,1,2,2,3,3-hexafluorocyclopentane having a boiling point of 87°–88° C. at 1013 mbar. The mass spectrum showed the molecular ion at m/e 178.

$n_D^{20}$: 1.309.

$^1$H—NMR (internal TMS standard): 2.25–2.5 ppm (m, 4H).

$^{19}$F—NMR (external $CF_3COOH$ standard): 36.5 ppm (tt, 4 F) and $-57.9$ ppm (m, 2F)

What is claimed is:

1. A process for preparing a fluorinated $C_4$ to $C_6$ hydrocarbon of the formula

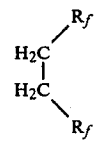

wherein $R_f$ is $CF_3$ or the two $R_f$ groups taken together are $-CF_2-CF_2-$, $-CF_2-CF_2-CF_2-$, or $CH(CF_3)-CH(CF_3)-$, comprising catalytically hydrogenating, in the presence of a base, an olefinic compound of the formula

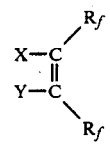

wherein
X is hydrogen, fluorine, chlorine, or bromine;
Y is fluorine, chlorine, or bromine; and
$R_f$ is defined as above.

2. A process according to claim 1 wherein the olefinic compound is 1,1,1,4,4,4-hexafluoro-2-chlorobutene, 3,3,4,4-tetrafluoro-1,2-dichlorocyclobutene, 3,3,4,4,5,5-hexafluoro-1,2-dichlorocyclopentene, 1,1,1,2,4,4,4-heptafluoro-2-butene,1,1,1,4,4,4- hexafluoro-2,3-dichlorobutene, or 1,1,1,4,4,4- hexafluoro-2-bromo-3-chlorobutene.

3. A process according to claim 1 wherein the base comprises an oxide, hydroxide, acetate, carbonate, or bicarbonate of an alkali metal; an oxide, hydroxide, acetate, carbonate, or bicarbonate of an alkaline earth metal; or a tertiary amine.

4. A process according to claim 1 wherein X is hydrogen.

5. A process according to claim 4 wherein 0.8 to 1.2 equivalents of base per mol of the olefinic compound is used.

6. A process according to claim 1 wherein X is chlorine.

7. A process according to claim 6 wherein 1.8 to 3 equivalents of base per mol of the olefinic compound is used.

8. A process according to claim 1 wherein the hydrogenation is performed at a pressure in the range of about 1 to 200 bar.

9. A process according to claim 1 wherein the hydrogenation is performed at a temperature in the range of about 0° to 200° C.

10. A process according to claim 1 wherein the olefinic compound of the formula

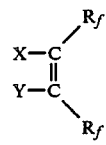

is prepared by a reaction comprising eliminating a hydrogen halide from a compound of the formula

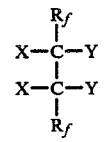

wherein at least one X is hydrogen.

* * * * *